US00PP32169P2

(12) United States Plant Patent
Lommerse et al.

(10) Patent No.: US PP32,169 P2
(45) Date of Patent: Sep. 8, 2020

(54) ***STACHYS* PLANT NAMED 'SUMMER SWEETS'**

(50) Latin Name: *Stachys officinalis*
Varietal Denomination: Summer Sweets

(71) Applicants: Gerardus Adrianus Petronella Lommerse, Noordwijkerhout (NL); Hendrikus Petrus Lommerse, Lisse (NL)

(72) Inventors: Gerardus Adrianus Petronella Lommerse, Noordwijkerhout (NL); Hendrikus Petrus Lommerse, Lisse (NL)

(73) Assignee: Future Plants Licentie B.V., Lisserbrock (NL)

( * ) Notice: Subject to any disclaimer, the term of this patent is extended or adjusted under 35 U.S.C. 154(b) by 0 days.

(21) Appl. No.: 16/602,184

(22) Filed: Aug. 23, 2019

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Stachys* plant named 'Summer Sweets', characterized by its compact and upright plant habit; moderately vigorous to vigorous growth habit; medium green-colored leaves; freely flowering habit; dense and relatively long inflorescences with light purplish pink-colored flowers; and good garden performance.

2 Drawing Sheets

Botanical designation: *Stachys officinalis*.
Cultivar denomination: 'SUMMER SWEETS'.

BACKGROUND OF THE INVENTION

The present invention relates to a new and distinct cultivar of *Stachys* plant, botanically known as *Stachys officinalis* and hereinafter referred to by the name 'Summer Sweets'.

The new *Stachys* plant is a product of a planned breeding program conducted by the Inventors in Lisserbroek, The Netherlands. The objective of the breeding program was to create new compact and freely-flowering *Stachys* plants with unique and attractive flower colors.

The new *Stachys* plant originated from a cross-pollination made by the Inventors in June, 2016 in Lisserbroek, The Netherlands, of *Stachys officinalis* 'Alba', not patented, as the female, or seed, parent with *Stachys officinalis* 'Rosea', not patented, as the male, or pollen, parent. The new *Stachys* plant was discovered and selected by the Inventors as a single plant from within the progeny of the stated cross-pollination in a controlled environment in Lisserbroek, The Netherlands in June, 2017.

Asexual reproduction of the new *Stachys* plant by divisions in a controlled environment in Lisserbroek, The Netherlands since August, 2017 has shown that the unique features of this new *Stachys* plant are stable and reproduced true to type in successive generations.

SUMMARY OF THE INVENTION

Plants of the new *Stachys* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Summer Sweets'. These characteristics in combination distinguish 'Summer Sweets' as a new and distinct *Stachys* plant:

1. Compact and upright plant habit.
2. Moderately vigorous to vigorous growth habit.
3. Medium green-colored leaves.
4. Freely flowering habit.
5. Dense and relatively long inflorescences with light purplish pink-colored flowers.
6. Good garden performance.

Plants of the new *Stachys* differ primarily from plants of the female parent, 'Alba', in plant habit as plants of the new *Stachys* are more compact than and shorter than plants of 'Alba'. In addition, plants of the new *Stachys* have light purplish pink-colored flowers whereas plants of 'Alba' have white-colored flowers.

Plants of the new *Stachys* differ primarily from plants of the male parent, 'Rosea', in plant habit as plants of the new *Stachys* are more compact than and shorter than plants of 'Rosea'. In addition, plants of the new *Stachys* have light purplish pink-colored flowers whereas plants of 'Rosea' have darker purple-colored flowers.

Plants of the new *Stachys* can be compared to plants of *Stachys officinalis* 'Ukkie', not patented. Plants of the new *Stachys* and 'Ukkie' differ primarily in the following characteristics:

1. Plants of the new *Stachys* have stronger stems than plants of 'Ukkie'.
2. Plants of the new *Stachys* have larger leaves than plants of 'Ukkie'.
3. Plants of the new *Stachys* have longer inflorescences than plants of 'Ukkie'.
4. Plants of the new *Stachys* have light purplish pink-colored flowers whereas plants of 'Ukkie' have lilac purple-colored flowers.

Plants of the new *Stachys* can also be compared to plants of *Stachys officinalis* 'Pink Cotton Candy', disclosed in U.S. Plant Pat. No. 21,436. Plants of the new *Stachys* and 'Pink Cotton Candy' differ primarily in the following characteristics:

1. Plants of the new *Stachys* are more compact and shorter than plants of 'Pink Cotton Candy'.
2. Plants of the new *Stachys* have light purplish pink-colored flowers whereas plants of 'Pink Cotton Candy' have light and bright pink-colored flowers.

BRIEF DESCRIPTION OF THE PHOTOGRAPHS

The accompanying colored photographs illustrate the overall appearance of the new *Stachys* plant showing the colors as true as it is reasonably possible to obtain in colored reproductions of this type. Colors in the photographs may differ slightly from the color values cited in the detailed botanical description which accurately describe the colors of the new *Stachys* plant.

The photograph on the first sheet is a side perspective view of typical flowering plant of 'Summer Sweets' grown in a container.

The photograph on the second sheet is a close-up view of a typical inflorescence of 'Summer Sweets'.

DETAILED BOTANICAL DESCRIPTION

The aforementioned photographs and following observations, measurements and values describe plants grown during the summer in 17-cm containers in an outdoor nursery in Lisserbroek, The Netherlands and under cultural practices typical of commercial *Stachys* production. During the production of the plants, day temperatures ranged from 18° C. to 30° C. and night temperatures ranged from 6° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Stachys officinalis* 'Summer Sweets'.

Parentage:

*Female, or seed, parent.*—*Stachys officinalis* 'Alba', not patented.

*Male, or pollen, parent.*—*Stachys officinalis* 'Rosea', not patented.

Propagation:

*Type*.—By softwood cuttings.

*Time to initiate roots, summer*.—About one month at ambient temperatures about 25° C.

*Time to produce a rooted young plant, summer*.—About three months at ambient temperatures about 20° C.

*Root description*.—Fine to medium in thickness, slightly fibrous; typically greyed white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a garden plant; compact and upright plant habit; moderately vigorous to vigorous growth habit; moderate growth rate; freely basal branching habit with about 15 primary basal branches developing per plant.

*Plant height, soil level to top of foliar plane*.—About 23.5 cm.

*Plant height, soil level to top of floral plane*.—About 32.4 cm.

*Plant width* (*spread*).—About 30.5 cm.

*Basal branches*.—Length: About 19.1 cm. Diameter: About 4 mm. Internode length: About 7.5 cm. Strength: Strong. Aspect: Upright to slightly outwardly. Texture and luster: Densely pubescent; longitudinally ridged; slightly glossy. Color, developing: Close to 144A to 144B. Color, developed: Close to 138A and 144A.

Leaf description:

*Arrangement*.—Opposite, simple.

*Length*.—About 7.5 cm.

*Width*.—About 3.2 cm.

*Shape*.—Narrowly ovate.

*Apex*.—Obtuse to broadly acute.

*Base*.—Truncate to hastate.

*Margin*.—Crenate.

*Texture and luster, upper surface*.—Densely pubescent, moderately rugose; slightly glossy.

*Texture and luster, lower surface*.—Densely pubescent, moderately rugose; matte.

*Venation pattern*.—Pinnate.

*Color*.—Developing leaves, upper surface: Close to 137A. Developing leaves, lower surface: Close to 138A. Fully expanded leaves, upper surface: Close to 137B; venation, close to 146C. Fully expanded leaves, lower surface: Close to between 146B and 147B; venation, close to 146D.

*Petioles*.—Length: About 3.3 cm. Diameter, flattened: About 1.5 mm to 2.5 mm. Texture and luster, upper and lower surfaces: Densely pubescent; moderately glossy. Strength: Strong. Color, upper and lower surfaces: Close to 144B.

Flower description:

*Flower type, arrangement and habit*.—Single tubular labiate flowers arranged on dense and relatively long terminal racemes; flowers sessile; freely flowering habit with about 270 flowers developing per inflorescence and about 4,000 flowers developing per plant during the flowering season; flowers with an upper lip and a three-lobed lower lip; flowers face mostly outwardly on the raceme.

*Natural flowering season*.—Plants flower for about ten weeks during the summer in The Netherlands.

*Flower longevity on the plant*.—Individual flowers last about one week on the plant; flowers not persistent.

*Fragrance*.—None detected.

*Flower buds*.—Length: About 9 mm. Diameter: About 3.5 mm. Shape: Oblong. Texture and luster: Densely pubescent; matte. Color: Close to 145B; distally, close to 146A.

*Inflorescence height*.—About 12 cm.

*Inflorescence diameter*.—About 3.7 cm.

*Flower diameter*.—About 5 mm.

*Flower length*.—About 1.1 cm.

*Flower throat diameter*.—About 2 mm.

*Flower tube length*.—About 9 mm.

*Flower tube diameter*.—About 3 mm.

*Petals*.—Quantity and arrangement: One upper lip and one three-lobed lower lip; lower 60% of the petals are fused into a narrow tube. Length, upper lip: About 1.5 cm. Length, lower lip: About 1.5 cm. Width, upper lip: About 4 mm. Width, lower lip: About 5 mm. Shape, upper and lower lips: Oblanceolate. Apex, upper lip: Obtuse. Apex, lower lip: Broadly emarginate. Margin, upper lip: Entire, not undulate. Margin, lower lip: Entire, moderately undulate; lateral lobes curved downward. Texture and luster, upper and lower lips, inner and outer surfaces: Smooth, glabrous, slightly velvety; matte. Texture and luster, throat: Smooth, glabrous; matte. Texture and luster, tube: Densely pubescent; matte. Color: When opening, upper and lower lips, inner surface: Close to 73C to 73D. When opening, upper lip, outer surface: Close to 73C. When opening, lower lip, outer surface: Close to 73C to 73D. Fully opened, upper lip, inner surface: Close to 75C; towards the apex, close to 75D. Fully opened, upper lip, outer surface: Close to 75C. Fully opened, lower lip, inner surface: Close to 68B and 68C. Fully opened, lower lip, outer surface: Close to 73C and 73D. Throat: Close to 73D. Tube: Close to between 73C and 75C; towards the base, close to NN155D.

*Sepals*.—Quantity and arrangement: Five, lower 70% fused into a campanulate calyx. Calyx length: About 7 mm. Calyx diameter: About 3 mm. Length: About 9 mm. Width: About 1.5 mm. Shape: Narrowly oblong. Apex: Acute. Margin: Entire. Texture and luster, upper surface: Smooth, glabrous; matte. Texture and luster, lower surface: Moderately pubescent; matte. Color: When opening, upper surface: Close to 145B; distally, close to 143A. When opening, lower surface: Close to 145B; distally, close to 146A. Fully opened, upper surface: Close to 143C; distally, close to 143A; at the apices, close to 69C. Fully opened, lower surface: Close to 138B; proximally, close to 145B; at the apices, close to 69C.

*Peduncles*.—Length: About 9.6 cm. Diameter: About 3 mm. Aspect: Mostly upright. Strength: Strong. Texture and luster: Densely pubescent; slightly glossy. Color: Close to 138A and 144A.

*Reproductive organs*.—Stamens: Quantity per flower: Four. Filament length: About 2 mm to 3 mm. Filament color: Close to 73D. Anther shape: Narrowly elliptic; dorsifixed. Anther size: About 0.5 mm by 1 mm. Anther color: Close to 163A. Pollen amount: Scarce. Pollen color: Close to NN155A. Pistils: Quantity per flower: One. Pistil length: About 1.1 cm. Stigma diameter: About 1 mm. Stigma shape: Cleft. Stigma color: Close to 68D. Style length: About 1 cm. Style color: Close to 68C; proximally, close to NN155D. Ovary color: Close to 152C.

*Seeds and fruits*.—To date, seed and fruit production have not been observed on plants of the new *Stachys*.

Pathogen & pest resistance: Plants of the new *Stachys* have not been observed to be resistant to pathogens and pests common to *Stachys* plants.

Garden performance: Plants of the new *Stachys* have exhibited good tolerance to rain, wind and temperatures ranging from about −29° C. to 35° C. and to be suitable for USDA Hardiness Zones 4 to 9.

It is claimed:

1. A new and distinct *Stachys* plant named 'Summer Sweets' as illustrated and described.

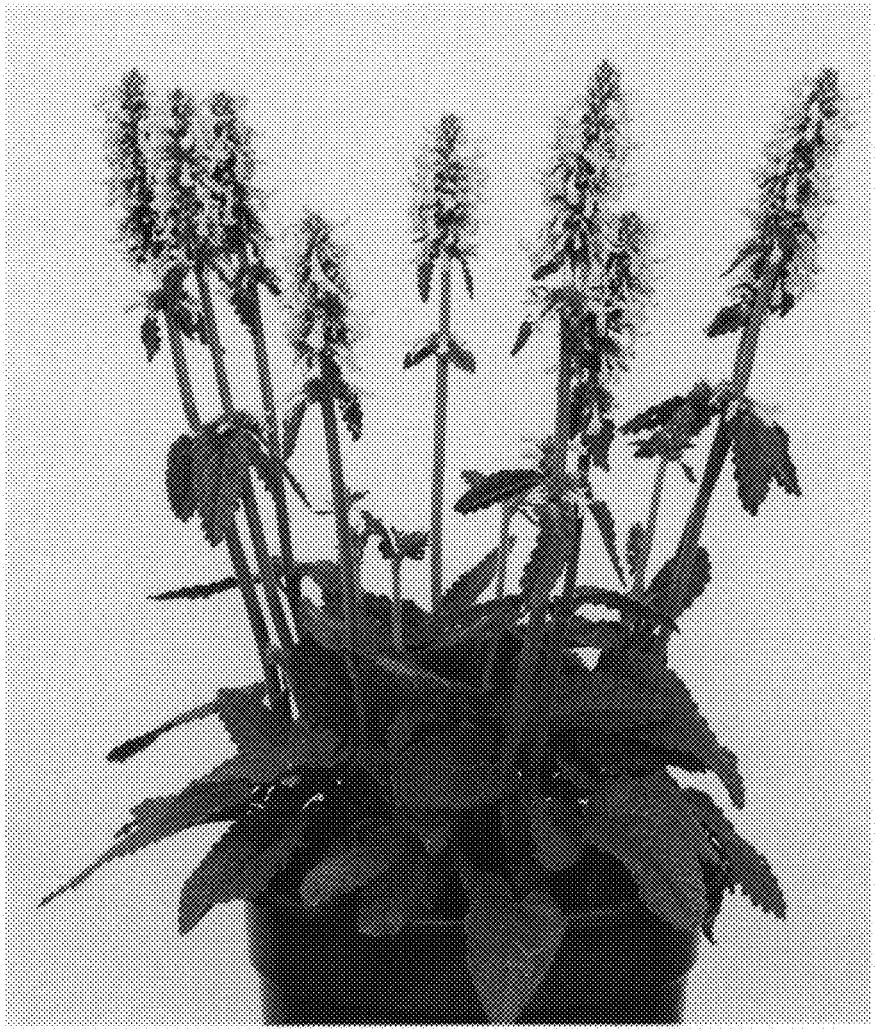

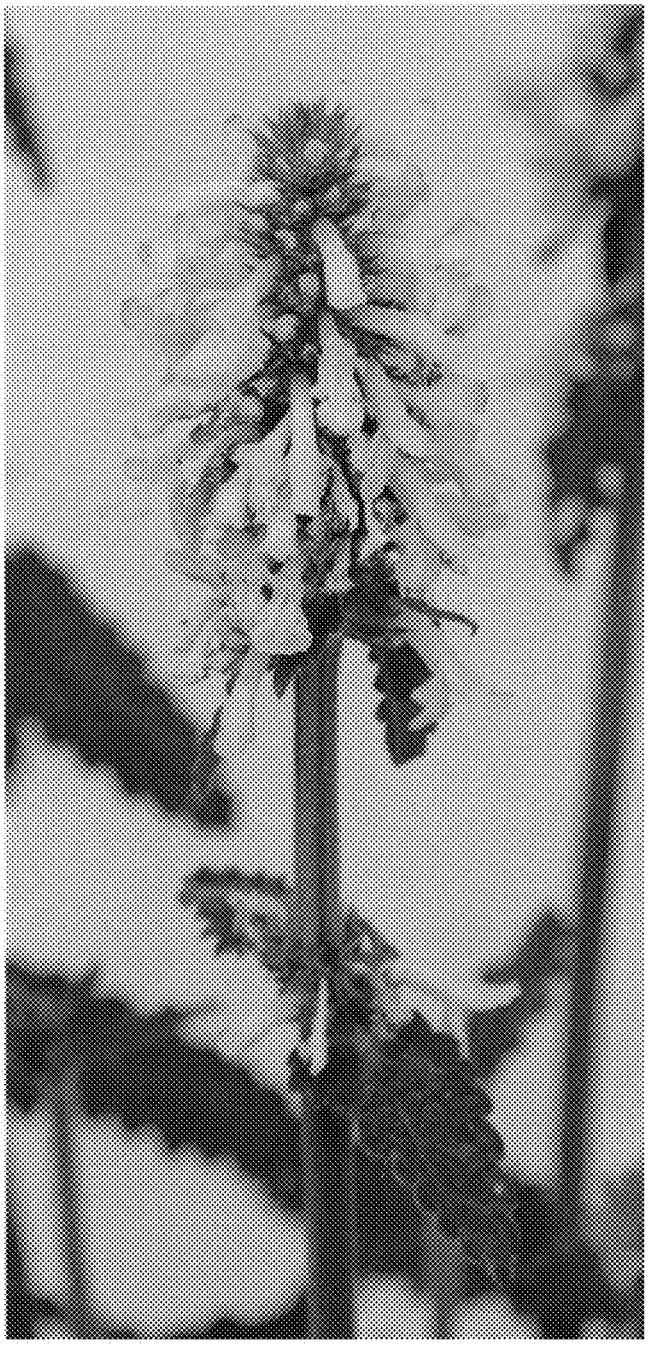

* * * * *